United States Patent [19]

Wiegers et al.

[11] 4,315,951
[45] Feb. 16, 1982

[54] FLAVORING WITH INDANE ALKANOLS AND TRICYCLIC ISOCHROMANS

[75] Inventors: Wilhelmus J. Wiegers, Red Bank; Mark A. Sprecker, Sea Bright; Hugh Watkins, Lincroft; Manfred H. Vock, Locust; Frederick L. Schmitt, Holmdel, all of N.J.

[73] Assignee: International Flavors & Fragrances Inc., New York, N.Y.

[21] Appl. No.: 212,886

[22] Filed: Dec. 4, 1980

Related U.S. Application Data

[63] Continuation-in-part of Ser. No. 63,518, Aug. 3, 1979, Pat. No. 4,265,818.

[51] Int. Cl.³ .............................................. A23L 1/226
[52] U.S. Cl. ..................................... 426/536; 426/538
[58] Field of Search ............................ 426/536, 538, 260/345.2

[56] References Cited

U.S. PATENT DOCUMENTS

| | | | |
|---|---|---|---|
| 3,360,530 | 12/1967 | Helringa et al. | 260/345.2 |
| 3,532,719 | 10/1970 | Thumer | 260/345.2 |
| 3,910,964 | 10/1975 | Sanders et al. | 260/345.2 |
| 3,978,090 | 8/1976 | Sanders et al. | 260/345.2 |
| 4,162,256 | 7/1979 | Sprecker et al. | 260/345.2 |
| 4,178,311 | 12/1979 | Sprecker et al. | 260/345.2 X |
| 4,250,200 | 2/1981 | Wiegers et al. | 426/536 |
| 4,265,818 | 5/1981 | Wiegers et al. | 426/536 X |

OTHER PUBLICATIONS

Furia et al., Fevaroli's Handbook of Flavor Ingredients, 2nd Ed., 1975. CRC Press: Cleveland, vol. I-p. 408; vol. II-p. 360.

Primary Examiner—Joseph M. Golian
Attorney, Agent, or Firm—Arthur L. Liberman

[57] ABSTRACT

Processes and compositions are described for the use in foodstuff flavor and aroma and perfume and perfumed article aroma augmenting, modifying, altering and enhancing compositions and as foodstuff, chewing gum, toothpaste, medicinal product, perfume and perfumed article aroma imparting materials of certain indane alkanols and tricyclic isochromans defined according to the generic structure:

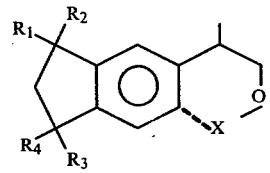

wherein one of $R_1$, $R_2$, $R_3$ or $R_4$ is $C_2H_5$ and the remaining $R_1$, $R_2$, $R_3$ and $R_4$ represents methyl; wherein X is —$CH_2$— or hydrogen and wherein the dashed line represents a carbon-carbon single bond or no bond with the proviso that when X is —$CH_2$—, then the dashed line is a carbon-carbon single bond and when X is hydrogen, the dashed line represents no bond.

Addition of said indane alkanols or said tricyclic isochromans or mixtures thereof is indicated to produce:

A. In food flavorings, a sweet, musky, patchouli-like, and ionone-like aroma and flavor characteristic; (useful for flavor augmentation or enhancement in pear, apricot and peach flavors);

B. In perfumes and perfumed articles, a sweet, musky aroma with earthy, minty and sweet nuances.

3 Claims, 8 Drawing Figures

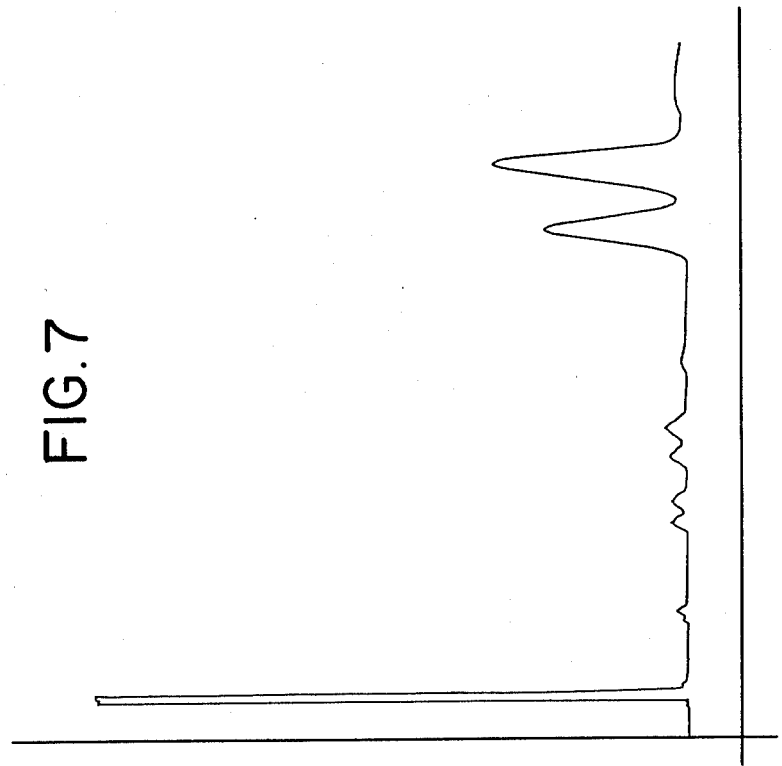
FIG. 7
GLC PROFILE FOR EXAMPLE IV
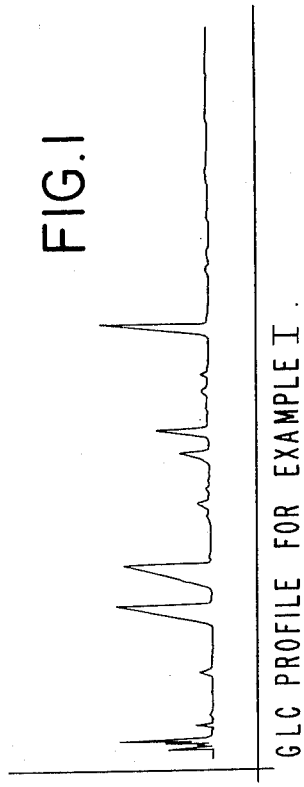
FIG. I
GLC PROFILE FOR EXAMPLE I.
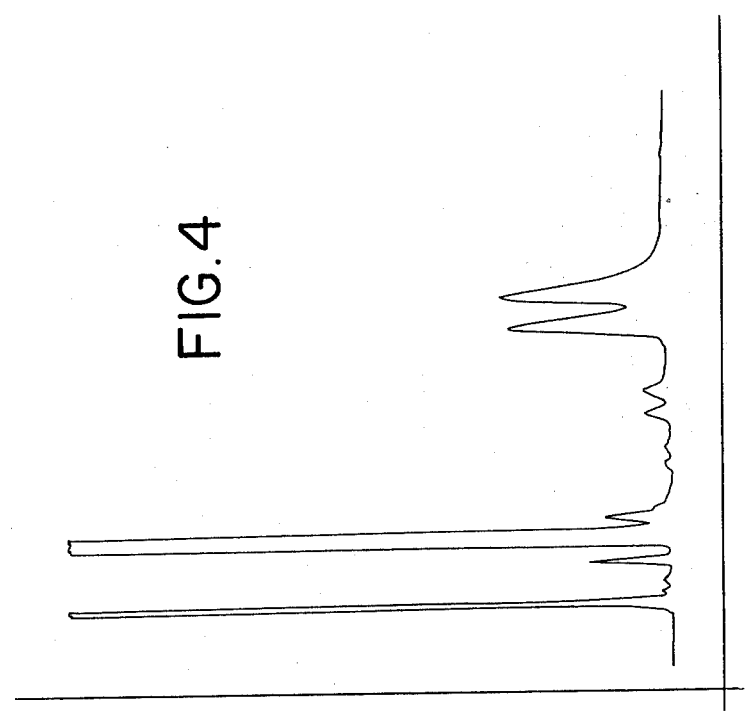
FIG. 4
GLC PROFILE FOR EXAMPLE II.

NMR SPECTRUM FOR EXAMPLE I.

IR SPECTRUM FOR EXAMPLE I.

NMR SPECTRUM FOR EXAMPLE II.

IR SPECTRUM FOR EXAMPLE II.

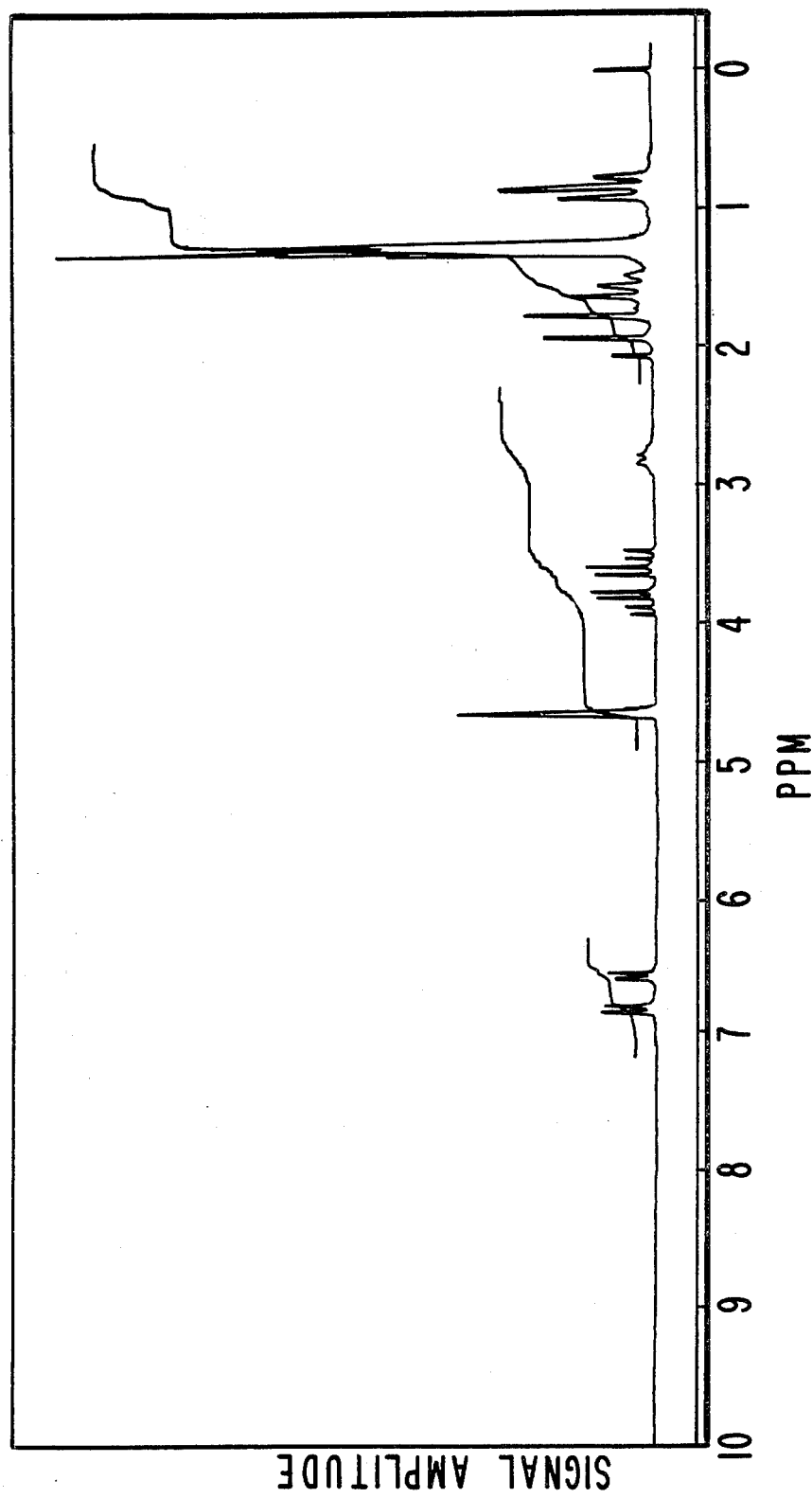

FLAVORING WITH INDANE ALKANOLS AND TRICYCLIC ISOCHROMANS

This application is a Continuation-in-Part of application for U.S. Letters Patent Ser. No. 063,518 filed on Aug. 3, 1979 now U.S. Pat. No. 4,265,818 issued on May 5, 1981.

BACKGROUND OF THE INVENTION

The present invention relates to indane alkanols and tricyclic isochromans and mixtures containing same as well as organoleptic uses thereof to alter, modify, augment, enhance or impart flavors and/or aromas in (or to) consumable materials.

There has been considerable work performed relating to substances which can be used to impart (or alter, modify or enhance) flavors and fragrances to (or in) various consumable materials. These substances are used to diminish the use of natural materials, some of which may be in short supply and to provide more uniform properties in the finished product. Sweet and musky aroma characteristics and sweet and musky flavor characteristics are particularly desirable for many uses in foodstuff flavors, particularly pear, apricot and peach flavors. Musky aromas are desirable in several types of perfume compositions and for use in perfumed articles.

The production of isochromans has been shown in the prior art and certain novel isochromans have recently been disclosed with an outstanding musk fragrance. Such isochromans especially adapted for perfumery by virtue of their fragrance properties have been disclosed in Heeringa and Beets, U.S. Pat. No. 3,360,530 issued on Dec. 26, 1967.

A number of routes have been shown to be available for the production of isochromans, such as those set forth in U.S. Pat. No. 3,360,530 and one of the most straight forward of these routes is treatment of a Friedel Crafts reactant with an alkylene oxide under Friedel Crafts conditions to form an aryl alkanol. The aryl alkanol is then isolated and thereafter reacted with formaldehyde to cyclialkylate the alcohol.

In addition, several other references set forth processes for the production of isochromans such as U.S. Pat. No. 3,532,719 and U.S. Pat. No. 3,910,964 as well as U.S. Pat. No. 3,978,090.

The aforementioned references set forth production of compounds having the structures:

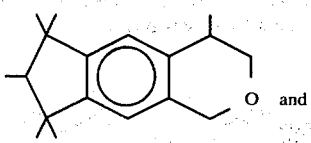

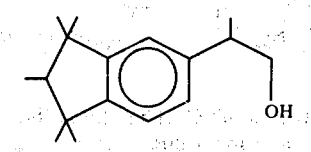

using as a precursor pentamethyl indane having the structure:

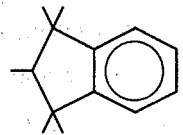

None of these references implies production of compounds having any of the structures:

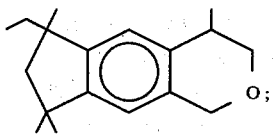

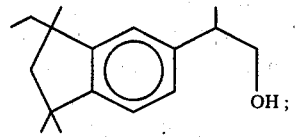

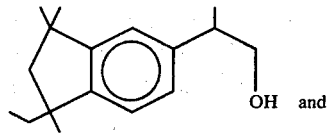

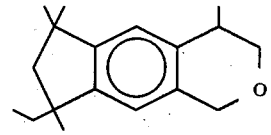

using as a precursor the tetraalkyl indane having the structure:

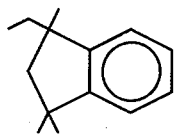

U.S. Pat. No. 3,400,159 issued on Sept. 3, 1968 entitled "Novel Musk-Like Substituted Acenaphthene and Process" discloses broadly at column 3, lines 42–61 that compounds having the formula:

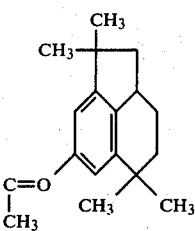

may be employed in "the same manner as other musk-like compounds alone or in admixture with other ingredients". It is further disclosed that such compounds may be used in perfumes, lotions, powders, soaps and the like containing one or more odorants or flavoring substances. The use of such compounds in foodstuffs, however, is not disclosed per se. Indeed, the statement that such compounds can be used "with other flavoring substances" is not preceded by an antecedent statement that there is utility of such compounds in flavoring or in augmenting, or enhancing the flavor of foodstuffs.

BRIEF DESCRIPTION OF THE DRAWINGS

FIG. 1 is the GLC profile for the hydrocarbon tetraalkylated and pentamethyl indane mixture produced according to Example I.

FIG. 4 is the GLC profile for the indane alkanol mixture produced according to Example II.

FIG. 7 is the GLC profile for the isochroman musk mixture produced according to Example III.

FIG. 8 is the NMR spectrum for the isochroman musk mixture produced according to Example III.

THE INVENTION

Figure 2:
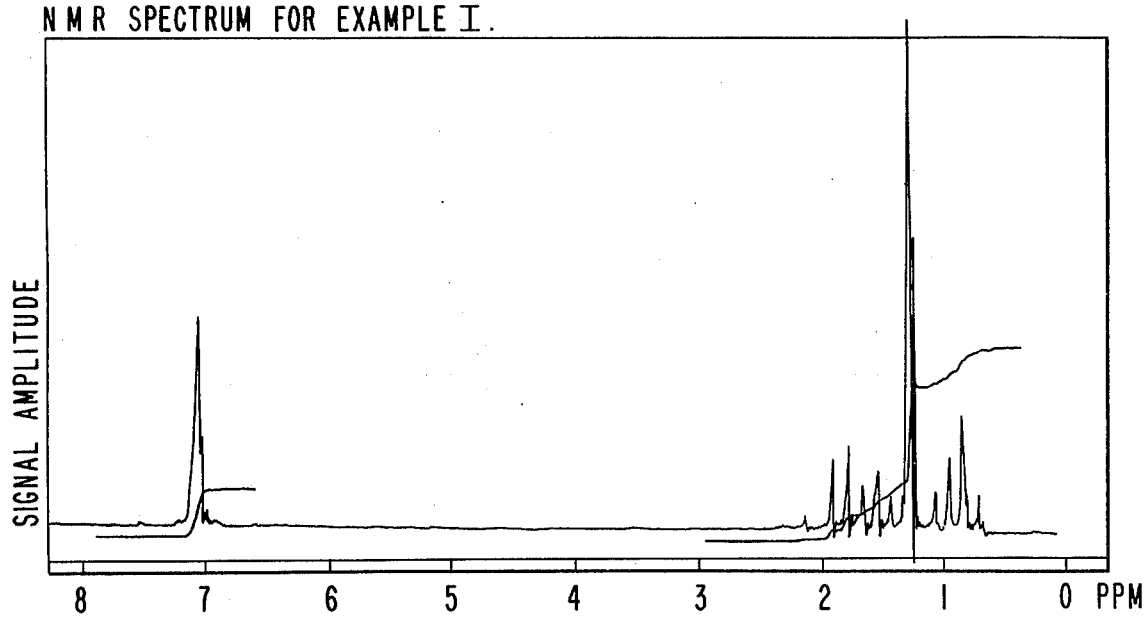
FIG. 2 is the NMR spectrum for the indane derivative mixture produced according to Example I.

It has now been discovered that novel solid and liquid foodstuff, chewing gum, medicinal product and flavoring compositions therefor having pear, peach and apricot flavors with sweet, musky aroma and flavor characteristics; and novel perfume compositions and perfumed articles having sweet, musky aromas with earthy and minty nuances may be provided by the novel indane alkanols and isochroman derivatives having the generic structure:

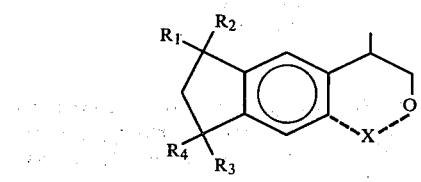

wherein one of $R_1$, $R_2$, $R_3$ and $R_4$ is ethyl and the remaining groups, $R_1$, $R_2$, $R_3$ and $R_4$ represent methyl; wherein X is —$CH_2$— or hydrogen; wherein the dashed line is a carbon-carbon single bond or represents no bond; with the proviso that when X is —$CH_2$—, then the dashed line is a carbon-carbon and when X is hydrogen, the dashed line represents no bond. More specifically, the compounds of our invention may be represented by the structures:

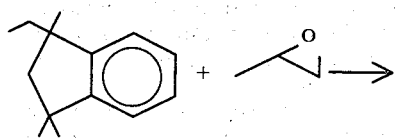

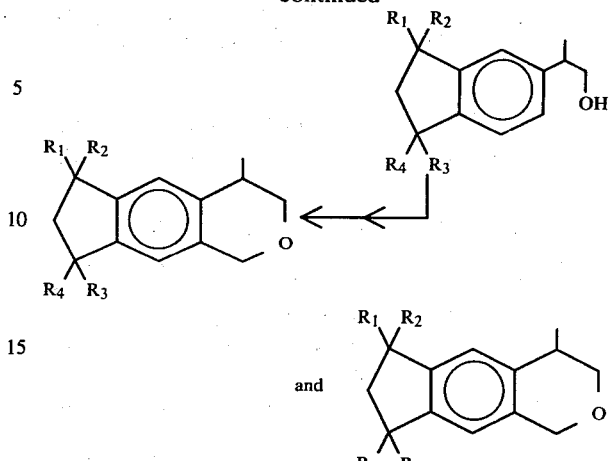

wherein $R_1$, $R_2$, $R_3$ and $R_4$ are defined as above.

The compounds of our invention may be first prepared by means of Diels Alder reaction of isoamylene to alpha methyl styrene according to the reaction:

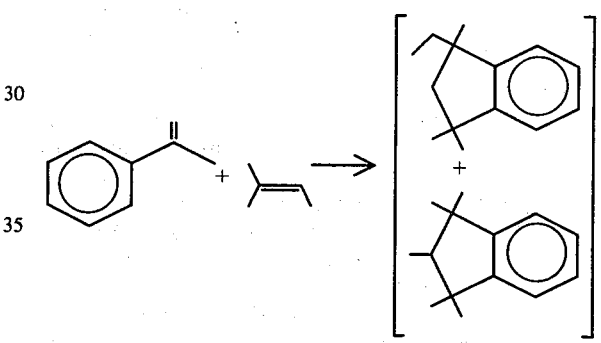

wherein surprisingly large quantities of the compound having the structure:

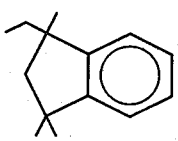

are produced. This reaction is carried out in the presence of a solid hetergeneous catalyst at high temperatures in a pressure apparatus. Depending upon the reaction conditions, the theoretical yield of the mixture of two products having the structures:

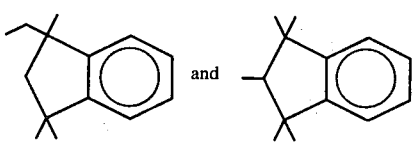

can vary from 30 up to 80%. The ratio of the two products produced varies according to the conditions used. The catalysts used should be acid clays, such as Filtrols ®, "SPA-2" ® (a Universal Oil Products catalyst which is phosphoric acid on clay) or acid ion exchange resins, such as Amberlyst 15 ® (produced by the Rohm & Haas Company, Philadelphia, Pa.) or Dowex ® 50 (produced by Dow Chemical Company, of Midland, Mich.). The mole ratio of the isoamylene to alpha methyl styrene should be between 1:1 and 2:1. The reaction can be carried out in the presence of or in the absence of a solvent and it is preferable that the reaction be carried out in the absence of solvent. When solvent is desired to be used, such solvents as aliphatic hydrocarbons and aliphatic chlorocarbons may be used, for example, methylene dichloride, hexane, n-heptane, n-octane, n-nonane, 2,4,4-trimethyl pentane and the like. The ratio of catalyst to reactants can vary between 0.1% and 8% of the total weight of alpha methyl styrene and isoamylene used. The reaction temperature can vary from 75° C. up to 250° C.; preferably between 100° and 200° C. The pressure for carrying out this reaction depends on the temperature of reaction and can vary from 50 psig to 300 psig. The reaction can be carried out batch-wise, continuous or semi-batch. In carrying out the batch process, solvent is first charged to the reactor (such as Primol ®) and the catalyst is then charged into a pressure vessel. Using a pressure pump, a mixture of amylene and alpha methyl styrene is pumped into the pressure vessel preheated to a specified temperature over a period of from 2 up to 10 hours. At the end of the feeding of the mixture, the vessel is stored in a quiescent state for a period of up to 5 hours. The pressure vessel is cooled and the catalyst is removed by filtration and the product is purified by distillation.

In a continuous process, a process rated tube is charged with catalyst and heated to the desired temperature. The mixture of amylene and alpha methyl styrene (and solvent, if desirable) is pumped through the tube and may be recycled several times. The resulting reaction is then distilled to yield the desired product.

The following table (Table I) indicates the results of carrying out batch reactions over a five-hour reaction time and five-hour age time. GLC peak I represents the compound having the structure:

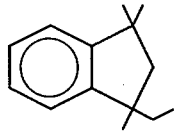

GLC peak II represents the compound having the structure:

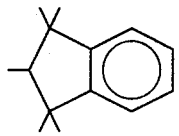

| Weight of Alpha Methyl Styrene | Weight of Amylene | Catalyst and gms. | Temp.° | GLC Results % Peak I | % Peak II |
|---|---|---|---|---|---|
| 590 | 400 | Filtrol 105 25 gm. | 175 | 29 | 24 |
| 590 | 400 | SPA-2 25 gm. | 175 | 28 | 25 |
| 590 | 400 | SPA-2 25 gm. | 150 | 25 | 28 |
| 590 | 400 | SPA-2 25 gm. | 125 | 12.5 | 30.5 |
| 590 | 400 | Si—Al 25 gm. | 150 | 25 | 41 |
| 590 | 400 | Si—Al 25 gm. | 125 | 6 | 15 |
| 590 | 400 | Filtrol 13 25 gm. | 100 | 24 | 33 |
| 590 | 400 | Filtrol 13 25 gm. | 100 | 26 | 28 |
| 590 | 400 | Filtrol 13 50 gm. | 125 | 28 | 26 |
| 590 | 400 | Filtrol 13 50 gm. | 125 | 28 | 29 |
| 590 | 400 | Filtrol 13 12.5 gm. | 125 | 24 | 29 |

The resulting of mixture of hydrocarbons having the structures:

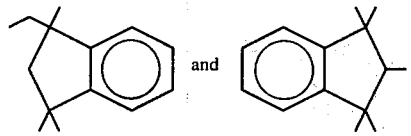

is then reacted with propylene oxide in the presence of a catalyst to produce the indane alkanols according to the reaction:

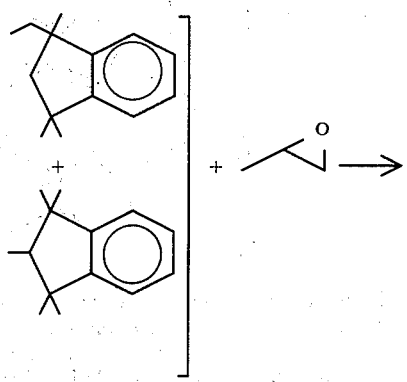

-continued

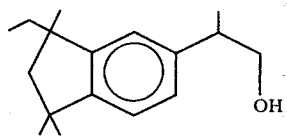
+
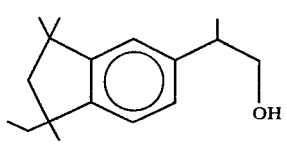
+
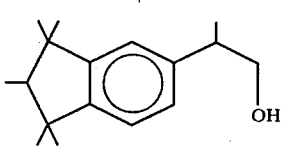

using the conditions of Example XV of U.S. Pat. No. 3,360,530 or the conditions of U.S. Pat. No. 3,532,719.

The resulting indane alkanol mixture may be separated or it may be used as is for its organoleptic properties in foodstuffs or in perfumery or it may be used as an intermediate in order to make the corresponding tricyclic isochroman derivative according to the reaction:

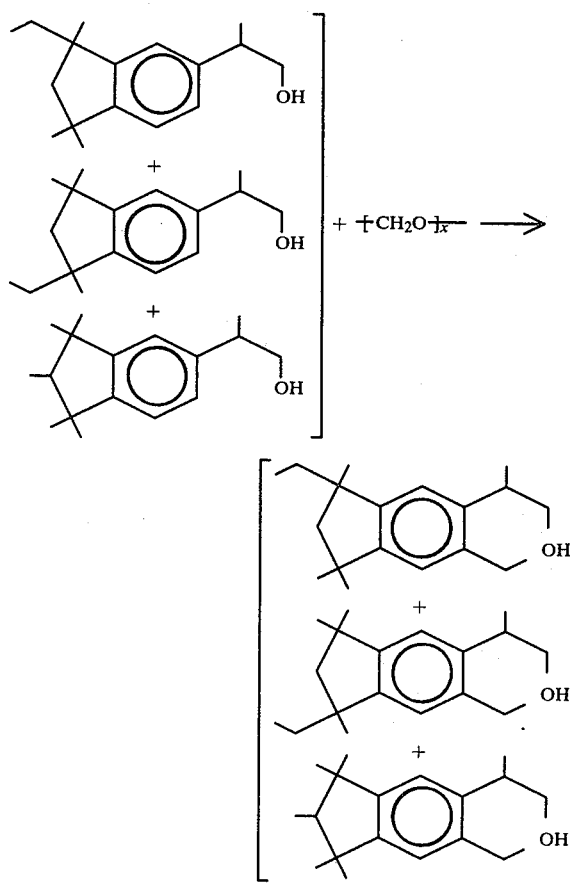

The conditions to carry out the cyclization to form the cyclic ethers are set forth in Example I of U.S. Pat. No. 3,910,964 issued on Oct. 7, 1975 or such reactions can be carried out according to Example I of U.S. Pat. No. 3,978,090 or according to Example XV of U.S. Pat. No. 3,360,530 (Part (c) at column 13, line 23).

The indane alkanols and tricyclic isochromans of our invention are capable of supplying and/or potentiating certain flavor and aroma notes usually lacking in many fruit flavors, particularly peach flavors, apricot flavors and pear flavors. Furthermore, the indane alkanols and tricyclic isochromans of our invention are capable of supplying certain fragrance notes usually lacking in many perfume materials, for example, musk fragrances. The indane alkanols and tricyclic isochromans of our invention have the following organoleptic properties:

TABLE II

| COMPOUND MIXTURE | ORGANOLEPTIC PROPERTIES |
|---|---|
| The mixture of compounds having the structures: | A musky aroma with some earthy, minty sweetness. |
| Mixture having the structures: | A sweet, musky aroma. |

TABLE III

| COMPOUND MIXTURE | ORGANOLEPTIC PROPERTIES |
|---|---|
| A mixture of compounds having the structures: | A patchouli, musky and ionone-like aroma and flavor profile at 1 ppm. |

TABLE III-continued

| | |
|---|---|
| A mixture of compounds having the structures: 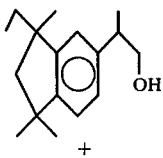 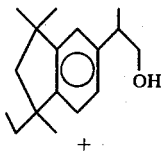 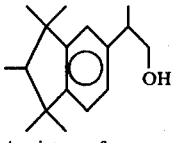 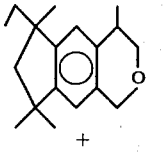 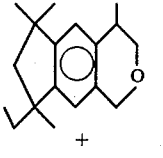 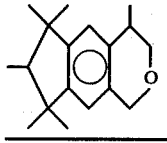 | A sweet, musky aroma and flavor characteristic having a potential use in pear, apricot and peach flavors at 1 ppm. |

When the indane alkanols and tricyclic isochromans of our invention are used as food flavor adjuvants, the nature of the co-ingredients included with said indane alkanols and tricyclic isochromans in formulating the product composition will serve to alter the organoleptic characteristics of the ultimate foodstuff treated therewith.

As used herein in regard to flavors, the terms "alter" and "modify" in their various forms means "supplying or imparting flavor character or note to otherwise bland, relatively tasteless substances or augmenting the existing flavor characteristic where a natural flavor or synthetic flavor or mixture of natural and synthetic flavors is deficient in some regard, or supplementing the existing flavor impression to modify its quality, character or taste".

As used herein, the term "enhance" is intended to mean the intensification (without effecting a change in kind of quality or aroma or taste) of one or more taste and/or aroma nuances present in the organoleptic impression of a consumable material, e.g., foodstuff, tobacco, chewing gum, medicinal product, perfume composition or perfumed article.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g., glycerine; and a flavoring composition which incorporates the indane alkanols and tricyclic isochromans of our invention, and, in addition, sweetening agents which may be sugars, including sucrose or dextrose and/or artificial sweeteners including dipeptides, cyclamates and saccharin. Other optional ingredients may also be present.

The term "medicinal product" includes both solids and liquids which are ingestible, non-toxic materials having medicinal value such as cough syrups, cough drops, toothpaste, aspirin and chewable medicinal tablets as further exemplified herein.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with the indane alkanols and tricyclic isochromans encompassed within the scope of our invention. Also critical is the additional requirement that such material be nonreactive (within the range of storage conditions and room temperature use conditions) with indane alkanols and tricyclic isochromans.

Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene, (2,6-di-tertiary-butyl-4-methyl phenol), propyl gallate and the like and sequestrants, e.g., citric acid.

Thickener compounds include carriers, binders, protective colloids, suspending agents, emulsifiers, and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins, and emulsifiers, e.g., mono- and diglycerides of fatty acids, skim silk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents, such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like, firming agents such as aluminum sodium sulfate, calcium chloride and calcium gluconate; texturizers, anti-caking agents, e.g., aliminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, cis and trans 2-methyl-2-pentenoic acid, and cis and trans 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptenal, 4-(p-hydroxyphenyl)-2-butanone, alpha-ionone, beta-ionone, methyl-3-butanone, 2-pentanone, 2-pentenal and propanal; alcohols such as 1-butanol, benzyl alcohol, 1-borneol, trans-3-buten-1-ol, ethanol, geraniol, 1-hexanol, 2-heptenol-1, trans-3-hexenol-1, cis-3-hexen-1-ol, 3-methyl-3-buten-1-ol, 1-penten-2-ol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, n-hexyl butyrate, isoamyl acetate, isopropyl butyrate, methyl acetate, methyl-n-butyrate, methyl caproate, methyl isobutyrate, alpha-methyl-n-butyrate, n-propyl acetate, n-amyl acetate, n-amyl-n- butyrate, benzyl salicylate, dimethyl anthranilate, ethyl methylphenylglycidate, ethyl succinate, isobutyl cinnamate, and terpenyl acetate; lactones, such as delta-decalactone, delta-undecalactone, delta-nonyl-lactone, gamma-undecalactone, gamma-dodecalactone and gamma nonyl-lactone as well as "peach" lactones; essential oils, such as jasmine absolute, rose absolute, orris absolute, lemon essential oil, Bulgarian rose, yara yara, natural raspberry oil and vanilla; sulfides, e.g., methyl sulfide and other materials such as maltol, acetoin, acetals (e.g., 1,1-diethoxyethane, 1,1-dimethoxyethane and dimethoxymethane) and 2- and 3- cyclotetradecene-1ones having one of the structures:

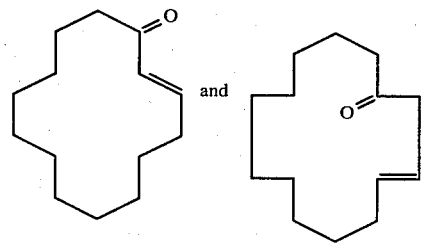

described in application for U.S. Letters Patent, Ser. No. 973,093 filed on Dec. 26, 1978.

The specific flavoring adjuvant selected for use may be either solid or liquid depending upon the desired physical form of the ultimate product, i.e., foodstuff whether simulated or natural, and should, in any event, be capable of providing an environment in which the indane alkanols and tricyclic isochromans can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of indane alkanols and tricyclic isochromans employed in a particular instance can vary over a relatively wide range whereby specific desired organoleptic effects (having particular reference to the nature of the product) are achieved. Thus, correspondingly greater amounts would necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify, or enhance the organoleptic characteristics of the parent composition, whether foodstuff per se or flavoring composition.

The use of insufficient quantities of indane alkanols and tricyclic isochromans will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it has been found that quantities of indane alkanols and tricyclic isochromans ranging from a small but effective amount, e.g., 0.0001 parts per million up to about 50 parts per million by weight based on total composition are suitable. Concentrations in excess of the maximum quantity stated are not normally recommended, since they fail to provide commensurate enhancement or augmentation of organoleptic properties. In those instances wherein the indane alkanols and tricyclic isochromans are added to the foodstuff as an integral component of a flavoring composition, it is, of course, essential that the total quantity of flavoring composition employed be sufficient to yield an effective concentration (of indane alkanols and tricyclic isochromans) in the foodstuff product.

Food flavoring compositions prepared in accordance with the present invention preferably contain the indane alkanols and tricyclic isochromans in concentrations ranging from about 0.01% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the indane alkanols and tricyclic isochromans with, for example, gum arabic, gum tragacanth, carrageenan and the like, and thereafter spray-drying the resultant mixture whereby to obtain the particulate solid product. Pre-prepared flavor mixes in powder form, e.g., a fruit-flavored powder mix are obtained by mixing the dried solid components, e.g., starch, sugar and the like and indane alkanols and/or tricyclic isochromans in a dry blender until the requisite degree of uniformity is achieved.

It is presently preferred to combine with indane alkanols and tricyclic isochromans, the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
β-Damascone;
β-Damascenone;
Ethyl butyrate;
Acetic acid;
n-Hexyl acetate;
n-Hexyl isobutyrate;
Trans-2-hexenal;
Linalyl isobutyrate;
n-Hexyl-2-methyl-n-butyrate;
Gamma-undecalactone;
Gamma-nonalactone;
Gamma-decalactone;
Delta undecalactone;
Delta dodecalactone;
Delta nonyl lactone;
"Peach" lactone;
Naphthyl ethyl ether;
Diacetyl;
Apple Fusel Oil;
Sauge Sclaree;
Coriander Oil;
Ethyl acetate;
Anethole;
Isoamyl-n-butyrate;
Ethyl-2-methyl-cis-3-pentenoate;
Cis-3-hexenol-1;
2-Methyl-cis-3-pentenoic acid;
2-Methyl-2-pentenoic acid;
Elemecine (4-allyl-1,2,6-trimethoxy benzene);
Isoelemecine (4-propenyl-1,2,6-trimethoxy benzene);
2-(4-hydroxy-4-methylpentyl) norbornadiene prepared according to U.S. Pat. 3,886,289; and
2- and 3-Cyclotetradecen-1-ones having the structures:

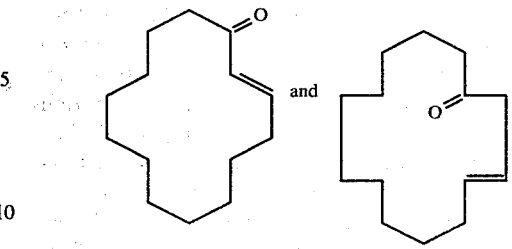

described according to application for U.S. Letters Patent, Ser. No. 973,093 filed on Dec. 26, 1978

The indane alkanols and tricyclic isochromans and one or more auxiliary perfume ingredients including, for example, alcohols other than the indane alkanols of our invention, aldehydes, nitriles, esters, cyclic esters, ketones, ethers other than the tricyclic isochromans of our invention, natural essential oils and synthetic essential oils may be admixed so that the combined odors of the individual components produce a pleasant and desired fragrance, particularly and preferably, in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to its particular olfactory characteristics, but the over-all effect of the perfume composition will be the sum of the effects of each of the ingredients. Thus, the indane alkanols and tricyclic isochromans can be used to alter the aroma characteristics of a perfume composition, for example, by utilizing or moderating the olfactory reaction contributed by at least one other ingredient in the composition.

The amount of indane alkanols and tricyclic isochromans of our invention which will be effective in perfume compositions depends on many factors including the other ingredients, their amounts and the effects which are desired. It has been found that perfume compositions containing as little as 0.01% of indane alkanols and tricyclic isochromans and even less (e.g, 0.005%) can be used to impart sweet, musky aromas with earthy and minty and sweet nuances to soaps, anionic, cationic and nonionic detergents, fabric softener articles and compositions of matter, cosmetics or other products. The amount employed can range up to 10% of the fragrance components and can range up to 0.5% of the weight of the perfumed article and will depend upon considerations of cost, nature of the end product, the effect desired on the finished product and the particular fragrance sought.

The indane alkanols and tricyclic isochromans are useful, taken alone or in perfume compositions as olfactory components in anionic, cationic and nonionic detergents, soaps, fabric softener compositions, fabric softener articles for use in clothes dryers (e.g., "BOUNCE" ®, a registered trademark of the Procter & Gamble Company of Cincinnati, Ohio), space odorants and deodorants, perfumes, colognes, toilet water, bath preparations, such as bath oils, and bath solids; hair preparations, such as lacquers, brilliantines, creams, deodorants, hand lotions and sun screens; powders, such as talcs, dusting powders, face powders and the like. When used as an olfactory component in perfume compositions or perfumed articles, such as anionic, cationic and nonionic detergents and in fabric softener compositions and fabric softener articles (e.g., for use in clothing dryers) as little as 0.05% of the indane alkanols and tricyclic isochromans of our invention will suffice to impart an intense sweet musk fragrance with earthy and minty nuances. Generally, no more than 5% of the indane alkanols and tricyclic isochromans based on the ultimate end product is required in the perfume composition or in the perfumed article.

In addition, the perfume composition or fragrance composition of our invention can contain a vehicle or carrier for the indane alkanols and tricyclic isochromans. The vehicle can be a liquid such as a non-toxic alcohol, a non-toxic glycol, or the like. The carrier can also be an absorbent solid, such as a gum (e.g., gum arabic) or components for encapsulating the composition (such as gelatin) as by means of coacervation.

It will thus be apparent that the indane alkanols and tricyclic isochromans of our invention can be utilized to alter the sensory properties, particularly organoleptic properties, such as flavors and/or fragrances of a wide variety of consumable materials.

The following examples are illustrative and the invention is to be considered restricted thereto only as indicated in the appended claims. All parts and percentages given herein are by weight unless otherwise specified.

EXAMPLE I

PREPARATION OF PENTAMETHYL INDANE AND TRIMETHYL ETHYL INDANE MIXTURE

Reaction:

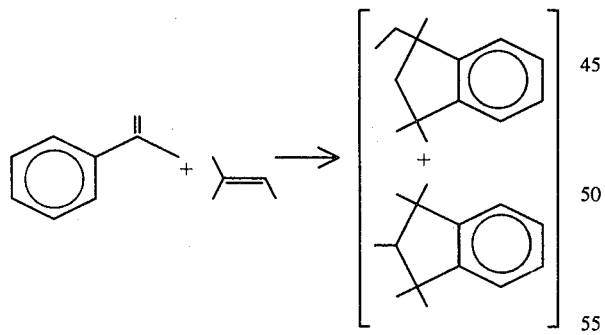

Into a two liter stirring autoclave (Parr) is charged 150 grams of Primol ® and 25 grams of Filtrol 13 ®. The autoclave is then flushed with nitrogen and heated to 125° C. 590 Grams of alpha methyl styrene and 400 grams of amylene in admixture is pumped into the autoclave over a period of five hours. The autoclave contents is then stirred for an additional five hours.

Five batches are combined and the catalyst is removed by filtration. The filtrate is distilled through a Goodloe packed column (8"×1½") at a reflux ratio 4:1:

| Fraction No. | Vapor Temp. | Liquid Temp. | Pressure mm. Hg. | Weight of Fraction (grams) |
|---|---|---|---|---|
| 1–6 | 64 | 125 | 50→4.8 | 273 |
| 7–11 | 63–70 | 110–116 | 3.8 | 374 |
| 12–25 | 70–74 | 116–139 | 3.8–4.6 | 1817 |
| 26 | 78 | 144 | 4.5 | 172 |
| 27–32 | 81–90 | 144–156 | 1.8 | 471 |
| 33–38 | 103–116 | 167–235 | 2.5 | 1091 |
| | | | Residue: | 215 |

GLC analysis shows the following:

Fractions 1–6: Mainly recovered C₅ hydrocarbons

Fractions 7–11: 11% Tetramethyl indane, 44% ethyl trimethyl indane and 31% pentamethyl indane Fractions 12–25: 46% Ethyl Trimethyl indane and 51% pentamethyl indane.

Fraction 26: 15% Ethyl trimethyl indane and 67% pentamethyl indane.

Fractions 27–32 and 33–38: Mainly trimers of amylene and dimers of alpha methyl styrene.

Fractions 7–26 represent a yield of approximately 5% of theory based on alpha methyl styrene.

FIG. 1 represents the GLC profile of the crude reaction product (Conditions: ¼"×10' 5% Carbowax packed column, operated 125° C., isothermal).

FIG. 2 represents the NMR spectrum for 3-ethyl-1,1,3-trimethyl indane.

Figure 3:
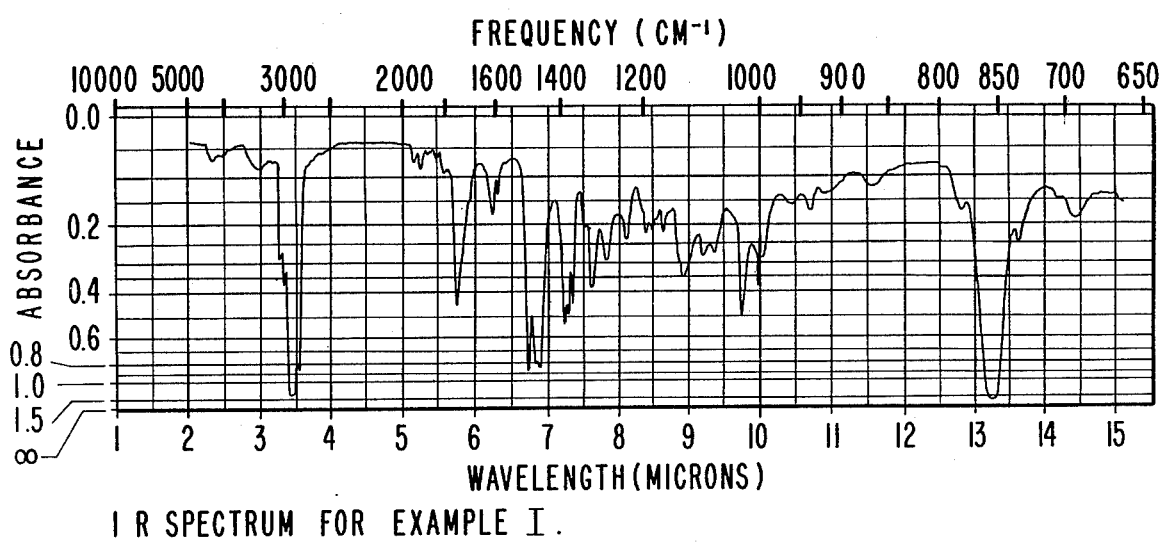
FIG. 3 is the infrared spectrum for the indane derivative mixture produced according to Example I.

FIG. 3 represents the infrared spectrum for 3-ethyl-1,1,3-trimethyl indane.

EXAMPLE II

PREPARATION OF A MIXTURE OF 3-ETHYL-ALPHA-1,1,3-TRIMETHYL-5(OR 6)-INDANE-1-METHYL-ETHANOL-2 AND 1,1,2,3,3-PENTAMETHYL-5-INDANE-1-METHYL-ETHANOL-2

Reaction:

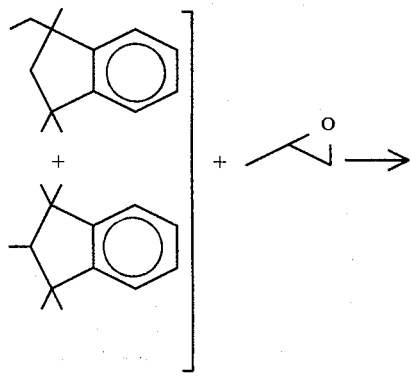

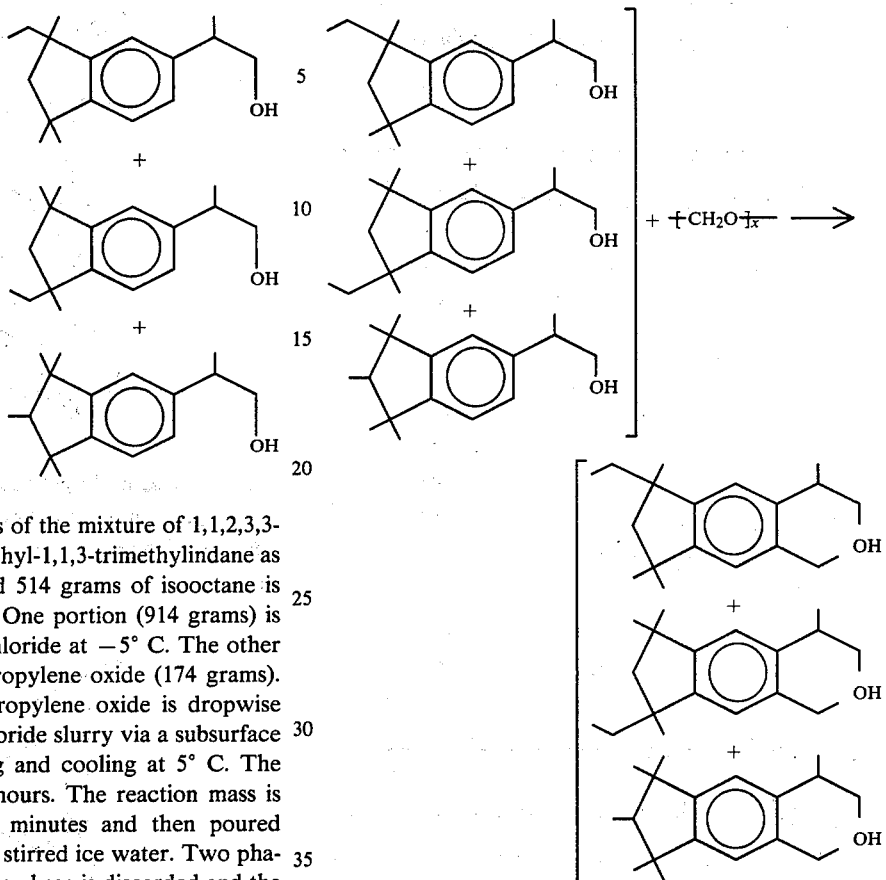

A solution of 1200 grams of the mixture of 1,1,2,3,3-pentamethylindane and 3-ethyl-1,1,3-trimethylindane as prepared in Example I and 514 grams of isooctane is divided into two portions. One portion (914 grams) is admixed with aluminum chloride at −5° C. The other portion is admixed with propylene oxide (174 grams). The solution containing propylene oxide is dropwise added to the aluminum chloride slurry via a subsurface feed with vigorous stirring and cooling at 5° C. The feed is complete in three hours. The reaction mass is stirred at −5° C. for 10 minutes and then poured quickly into 4 liters of well stirred ice water. Two phases are formed. The aqueous phase is discarded and the organic phase is washed twice with water and once with 5% sodium carbonate solution. Distillation through a short column affords recovered isooctane, recovered pentamethyl and ethylmethyl indane mixture and 300 grams of a product mixture containing 3-ethyl-alpha-1,1,3-trimethyl-5(or 6)-indane-1-methyl-ethanol-2 1,1,2,3,3-pentamethyl-5-indane-1-methyl-ethanol-2. This material is further purified by fractional redistillation through a 1"×12" Goodloe packed column (130° C. to 142° C. at 1.7 mm. Hg. pressure).

FIG. 4 is the GLC trace of the crude reaction mass (¼"×10', SE-30 packed column, 220° C., isothermal).

Figure 5:
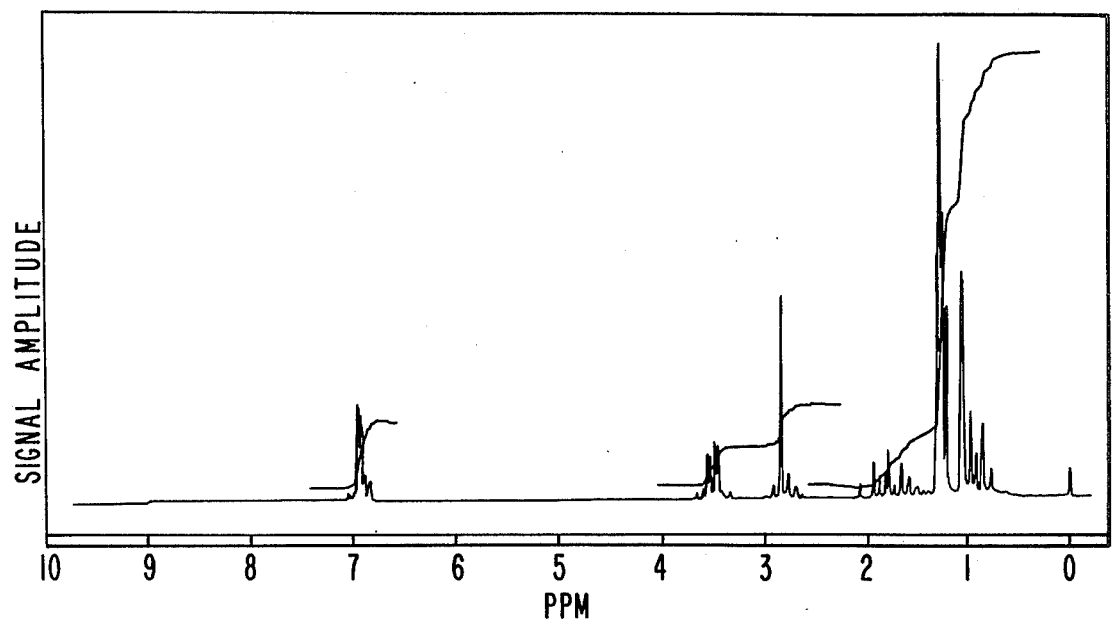
FIG. 5 is the NMR spectrum for the indane alkanol mixture produced according to Example II.

FIG. 5 represents the NMR spectrum of Fraction 4 of the redistillation.

Figure 6:
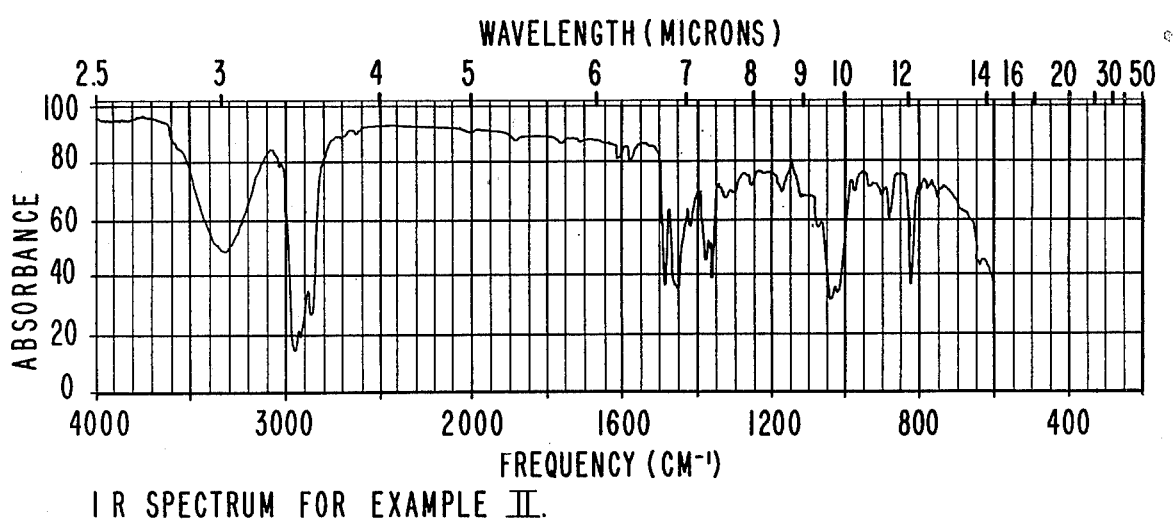
FIG. 6 is the infrared spectrum for the indane alkanol mixture produced according to Example II.

FIG. 6 represents the IR spectrum of Fraction 4 of the redistillation.

EXAMPLE III

PREPARATION OF A MIXTURE OF
6-ETHYL-1,3,4,6,7,8-HEXAHYDRO-4,6,8,8-TETRAMETHYLCYCLOPENTA[G]-2-BENZOPYRAN,
8-ETHYL-1,3,4,6,7,8-HEXAHYDRO-4,6,6,8-TETRAMETHYLCYCLOPENTA[G]-2-BENZOPYRAN
AND
1,3,4,6,7,8-HEXAHYDRO-4,6,6,7,8,8-HEXAMETHYLCYCLOPENTA[G]-2-BENZOPYRAN

Reaction:

A stirred slurry of the indene-1-methyl-ethanol-2 mixture is prepared in Example II (150 grams), para-toluene, sulfonic acid (20 grams), isopropyl alcohol (65 grams) and paraformaldehyde (21 grams) is heated to 93° C. (reflux) for three hours. The mass is then heated to 150° C. with concurrent removal of lower boiling materials by distillation. The reaction mass is stirred three hours at 150° C., then cooled to 80° C. Toluene (100 mls) and 200 mls of 5% sodium hydroxide solution are added thereto with stirring. The mass is cooled and the aqueous (lower) layer is washed with water and distilled through a sheet column to afford 147 grams of crude reaction product containing 6-ethyl-1,3,4,6,7,8-hexahydro-4,6,8,8-tetramethylcyclopenta[G]-2-benzoyran, 8-ethyl-1,3,4,6,7,8-hexahydro-4,6,6,8-tetramethylcyclopenta[G]-2-benzopyran and 1,3,4,6,7,8-hexahydro-4,6,6,7,8,8-hexamethylcyclopenta[G]-2-benzopyran. Redistillation through a 1"×12" Goodloe packed column affords the mixture with sufficient purity to be used in fragrance compositions (b.p. 117° C. at 1.2 mm. Hg. pressure).

FIG. 7 is the GLC trace of the crude reaction mass.

FIG. 8 is the NMR spectrum of 6-ethyl-1,3,4,6,7,8-hexahydro-4,6,8,8-tetramethylcyclopenta[G]-2-benzopyran and 8-ethyl-1,3,4,6,7,8-hexahydro-4,6,6,8-tetramethylcyclopenta[G]-2-benzopyran.

—$(CH_2O)_x$— represents standard nomenclature for paraformaldehyde wherein x is a number greater than 1 since paraformaldehyde is a mixture of formaldehyde and dimers and higher polymers of formaldehyde.

EXAMPLE IV

The following basic pear flavor formulation is prepared:

| Ingredients | Parts by Weight |
|---|---|
| Vanillin | 2.0 |
| Hexyl acetate | 8.0 |
| Hexyl isobutyrate | 20.0 |
| Trans-2-hexenal (10% in propylene glycol) | 2.0 |
| n-Hexanal | 0.5 |
| Apple Fusel Oil | 10.0 |
| Linalyl Isobutyrate | 0.5 |
| Hexyl-2-methylbutyrate | 10.0 |
| Sauge Sclaree (10% in propylene glycol) | 0.5 |
| Coriander Oil | 0.5 |
| Food grade ethyl alcohol (aqueous, 95%) | 146.0 |
| Propylene glycol | 800.0 |

To a portion of the above basic pear flavor formulation, 0.02% by weight of a mixture containing the following ingredients:

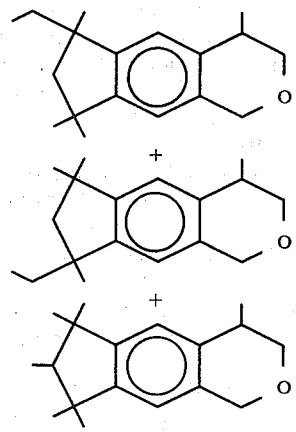

produced according to Example III is added. To another portion of the basic pear flavor formulation, nothing is added. Both flavor formulations are compared at the rate of 50 ppm in water and evaluated by a bench panel of four experienced tasters. All the tasters of the bench panel state that the flavor containing the mixture of compounds having the structures:

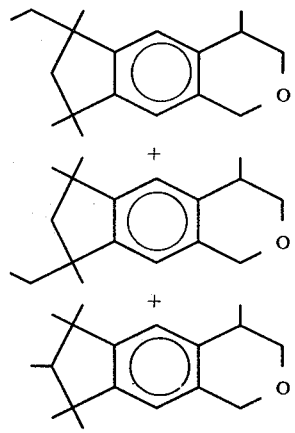

has a more natural riper pear character. This pear character is enhanced and longer lasting as a result of the addition of the mixture of compounds having the structures:

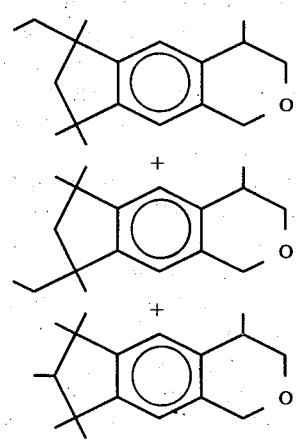

Therefore the flavor formulation containing the compounds having the structures:

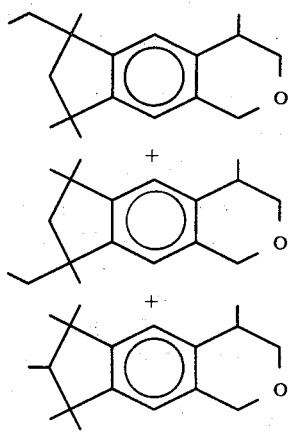

is preferred.

EXAMPLE V

Granular detergent compositions prepared according to United Kingdom Patent Specification No. 1,501,498 having the following formulae are prepared by spray-drying the following mixtures as indicated in the columns headed V A, V B, V C and V D.

| Ingredient | COMPOSITION IN % BY WEIGHT | | | |
|---|---|---|---|---|
| | Example VA | Example VB | Example VC | Example VD |
| Sodium salt of ethoxylated fatty alcohol sulfate | 14.1 | 14.1 | 14.1 | 14.1 |
| $Na_{12}(AlO_2 \cdot SiO_2)_{12} \cdot 27H_2O$ | 18.0 | 18.0 | 18.0 | 18.0 |
| Moisture | 10.0 | 10.1 | 9.9 | 10.2 |
| Sodium sulfate | 25.0 | 25.0 | 20.0 | 20.0 |
| Minor ingredients including sodium toluene sulfonate, trisodium sulfosuccinate, dyes, and brighteners | 4.0 | 2.4 | 3.6 | 2.3 |

| Ingredient | COMPOSITION IN % BY WEIGHT | | | | | |
|---|---|---|---|---|---|---|
| | Example VA | Example VB | Example VC | Example VD | Example VE | Example VF |
| Indane alkanol mixture prepared according to Example II | 1.5 | 0.0 | 0.0 | 0.0 | 0.0 | 0.0 |
| Compound having the structure: 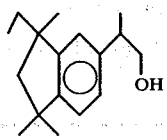 | 0.0 | 2.0 | 0.0 | 0.0 | 0.0 | 0.0 |
| Compound having the structure: 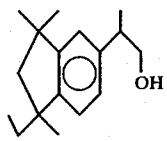 | 0.0 | 0.0 | 2.0 | 0.0 | 0.0 | 0.0 |
| Mixture of tricyclic isochromans having the structures: 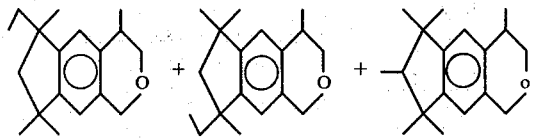 prepared according to Example III. | 0.0 | 0.0 | 0.0 | 3.0 | 0.0 | 0.0 |
| Compound having the structure:  | 0.0 | 0.0 | 0.0 | 0.0 | 3.0 | 0.0 |
| Compound having the structure: 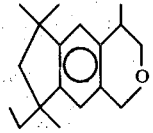 | 0.0 | 0.0 | 0.0 | 0.0 | 0.0 | 3.0 |
| having an average of about 2.25 moles of ethylene oxide per mole of fatty alcohol | | | | | | |
| Sodium tallow alkyl sulfate | 2.4 | 2.4 | 2.4 | 2.4 | | |
| Sodium silicate solids ratio: $SiO_2/Na_2O = 2.0$ | 0.0 | 2.0 | 6.0 | 0.0 | | |
| Sodium silicate solids ratio: $SiO_2/Na_2O = 3.2$ | 1.0 | 0.0 | 0.0 | 6.0 | | |
| Sodium tripolyphosphate | 24.0 | 24.0 | 24.0 | 24.0 | | |

Laundry solutions containing the above detergent compositions are used to launder fabrics. Each of the laundry compositions both prior to and on laundering gives rise to an intense musk aroma.

Each of the compositions of Examples VA, VB and VC has a sweet, musk aroma in addition to having earthy and minty nuances. Each of the compositions of Examples VD, VE and VF have a sweet, musk aroma also.

EXAMPLE VI

PERFUMED LIQUID DETERGENT

Concentrated liquid detergents with animal-musky aromas are prepared containing 0.10%, 0.15% and 0.20% of tricyclic isochromans prepared according to Example III having the structures:

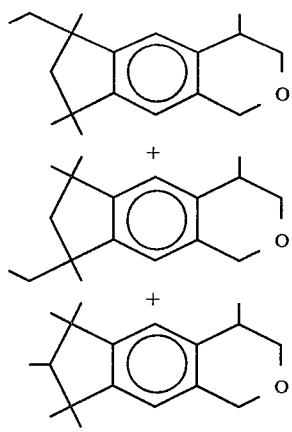

They are prepared by adding and homogeneously admixing the appropriate quantity of tricyclic isochromans in liquid detergent. The liquid detergent is a builder-free liquid detergent consisting of (a) 50% of a nonionic surfactant having an HLB of 8.0 and a critical micelle concentration of 0.007, weight % at 25° C.; (b) an ionic surfactant which is triethanolamine citrate; and (c) 1 weight % of diethanolamine prepared according to United Kingdom Patent Specification No. 1,491,603.

The detergents all possess sweek musky fragrances, the intensity increasing with greater concentrations of tricyclic isochromans.

EXAMPLE VII

A. POWDER FLAVOR

20 Grams of the flavor composition of Example IV which flavor composition contains a mixture of tricyclic isochromans is emulsified in a solution containing 300 grams gum acacia and 700 grams water. The emulsion is spray-dried with a Bowen Lab Model Drier utilizing 250 c.f.m. of air with an inlet temperature of 500° F., and outlet temperature of 200° F. and a wheel speed of 50,000 r.p.m.

B. PASTE BLEND

The following mixture is then prepared:

| Ingredients | Parts by Weight |
|---|---|
| Liquid Flavor Composition of Example IV | 48.4 |
| Cab-O-Sil M-5 (Brand of Silica produced by the Cabot Corporation of 125 High Street, Boston, Mass., 02110); Physical Properties: Surface Area: 200m²/gm Nominal Particle Size: 0.012 microns Density: 2/3 lbs./cu. ft. | 3.2 |

The Cab-O-Sil is dispersed in the liquid flavor composition with vigorous stirring, thereby resulting in a viscous liquid. 48.4 Parts by weight of the powder flavor composition prepared in Part A is then blended into the said viscous liquid, with stirring at 25° C. for a period of 30 minutes, resulting in a thixotropic sustained release flavor paste.

EXAMPLE VIII

CHEWING GUM

100 Parts by weight of chicle are mixed with 4 parts by weight of the flavor prepared in accordance with Example VII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.0 inches in thickness. The strips are cut into lengths of 3 inches each. On chewing, the chewing gum has a pleasant long-lasting pear flavor.

EXAMPLE IX

TOOTHPASTE FORMULATION

The following separate groups of ingredients are prepared:

| Group "A" | |
|---|---|
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate (foaming agent) |
| Group "D" | |
| 1.200 | Flavor Material of Example VII |
| 100.00 (TOTAL) | |

PROCEDURE
1. To ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sacrosinate.
5. The resultant slurry is then blended for one hour. The completed paste is then transferred to a three roller mill and then homogenized, and finally tubed.

The resulting toothpaste when used in a normal toothbrushing procedure yields a pleasant pear flavor of constant strong intensity throughout said procedure (1–1.5 minutes).

EXAMPLE X

CHEWABLE VITAMIN TABLETS

The flavor material produced according to the process of Example VII is added to a Chewable Vitamin Tablet Formulation at a rate of 5 gm/kg which Chewable Vitamin Tablet Formulation is prepared as follows:

| Ingredients | Gms/1000 Tablets |
| --- | --- |
| Vitamin C (ascorbic acid) as ascorbic acid solution mixture 1:1 | 70.0 |
| Vitamin $B_1$ (thiamine mononitrate) as Rocoat ® thiamine mononitrate 33% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxide hydrochloride 33⅓% | 4.0 |
| Niacinamide as Rocoat ® niacinamide 33⅓% | 33.0 |
| Calcium pantothenate | 11.5 |
| Vitamin $B_{12}$(cyanocoablamin) as Merck 0.1% in gelatin | 3.5 |
| Vitamin E(dl-alpha tocopheryl acetate) as dry Vitamin E acetate 33⅓% Roche | 6.6 |
| d-Biotin | 0.044 |
| Certified lake color | 5.0 |
| Flavor of Example VII | 5.0 |
| Sweetener - sodium saccharin | 1.0 |
| Magnesium stearate lubricant | 10.0 |
| Mannitol q.s. to make | 500.0 |

Preliminary tablets are prepared by slugging, with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablet yields a pleasant, long-lasting, consistently strong pear flavor for a period of 12 minutes.

EXAMPLE XI

MUSK PERFUME FORMULATION

The following musk perfume formulation is prepared:

| Ingredients | Parts by Weight |
| --- | --- |
| Musk Ambrette | 200 |
| Musk Ketone | 200 |
| Beta Ionone | 50 |
| Vetiveryl Acetate | 50 |
| Sandalwood Oil | 100 |
| Benzyl Benzoate | 400 |
| Mixture of indane alkanols prepared according to Example II | 20 |

The mixture of indane alkanols of Example II imparts to this musk formulation, a natural "animal-musk" aroma and causes it to be more "natural-like".

EXAMPLE XII

PREPARATION OF A SOAP COMPOSITION

100 Grams of soap chips are mixed with 1 gram of the perfume composition of Example XI until a substantially homogeneous composition is obtained. The perfumed soap composition manifests an excellent animal-musk aroma.

EXAMPLE XIII

PREPARATION OF A SOAP COMPOSITION

100 Grams of soap chips are mixed with 1 gram of the tricyclic isochroman mixture prepared according to Example III until a substantially homogeneous composition is obtained. The perfumed soap composition manifests an excellent musk aroma.

EXAMPLE XIV

PREPARATION OF A COLOGNE AND HANDKERCHIEF PERFUME

The mixture of tricyclic isochromans prepared according to Example III is incorporated into a cologne at concentrations of 1.5%, 2.0%, 2.5%, 3.0%, 3.5% and 4.0% in 85% aqueous ethanol; and into handkerchief perfumes at concentrations of 15%, 20%, 25% and 30% (in 95% aqueous ethanol). Distinct and definite animal-musk fragrances are produced and imparted to the cologne and to the handkerchief perfume at each of the levels indicated.

EXAMPLE XV

PREPARATION OF A COSMETIC POWDER COMPOSITION

A cosmetic powder is prepared by mixing in a ball mill, 100 grams of talcum powder with 0.15 grams of the mixture of indane alkanols prepared according to Example II. The resulting powder has an excellent musk aroma.

EXAMPLE XVI

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of the mixture of tricyclic isochromans having the structures:

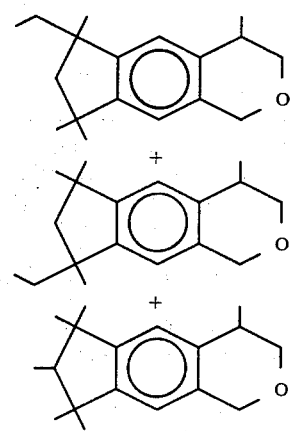

prepared according to Example III.

Fabric-softening compositions prepared as set forth above having an aroma characteristic which can be described as sweet and musky with exaltone-like nuances essentially consist of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. A sweet, musky, exaltone-like aroma is imparted in a pleasant manner to the head space in the dryer on operation thereof using the said dryer added fabric softening nonwoven fabric.

EXAMPLE XVIII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1.5 percent of the mixture of indane alkanols having the structures:

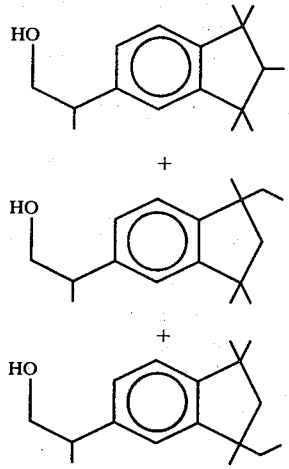

prepared according to Example II.

A fabric-softening composition prepared as set forth above having an aroma characteristic which can be described as sweet, musky and exaltone-like essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and an outer coating weight ratio of about 1:1 by weight of the substrate. The resulting aroma is described as sweet, musky and exaltone-like and is imparted in a pleasant manner to the head space in the dryer on operation thereof using the said dryer added fabric softening nonwoven fabric.

EXAMPLE XIX

PREPARATION OF A SOAP COMPOSITION

100 Grams of soap chips are prepared according to Example V of U.S. Pat. No. 4,058,490, issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide".

The resulting blend is then mixed with 1 gm of the compound having the structure:

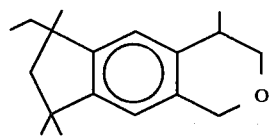

until a substantially homogeneous composition is obtained. The perfumed soap composition manifests an excellent sweet, musk, exaltone-like aroma.

EXAMPLE XX

PREPARATION OF A SOAP COMPOSITION

100 Grams of soap chips are prepared according to Example V of U.S. Pat. No. 4,058,490, issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide".

The resulting blend is then mixed with 1 gm of the compound having the structure:

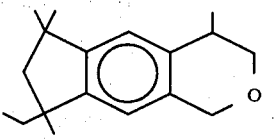

until a substantially homogeneous composition is obtained. The perfumed soap composition manifests an excellent musk aroma.

What is claimed is:

1. A process for augmenting or enhancing the aroma or taste of a foodstuff comprising the step of adding to said foodstuff from 0.0001 parts per million up to about 50 parts per million by weight based on the foodstuff of a product consisting essentially of compounds having the structures:

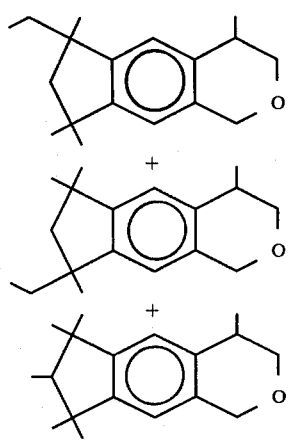

+ produced according to the process comprising the steps of (i) reacting isoamylene with alpha methyl styrene according to the reaction:

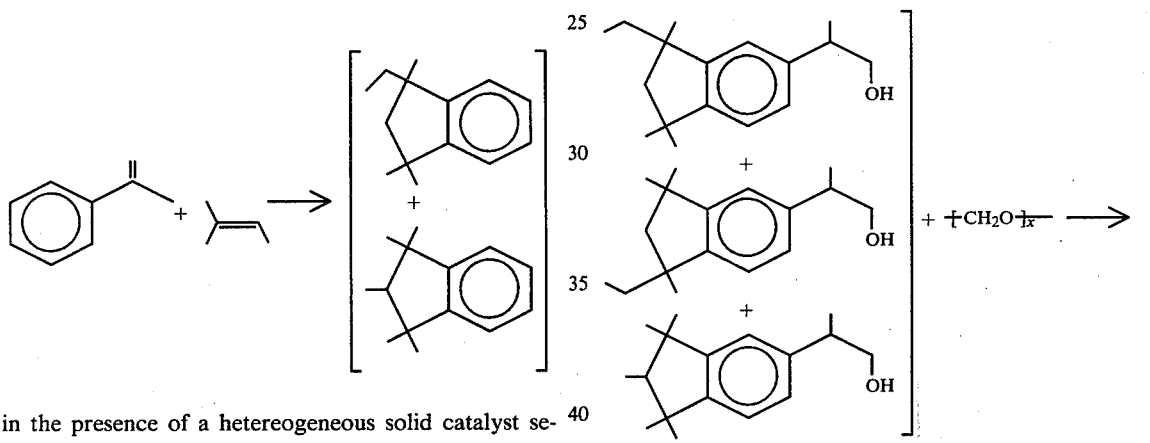

in the presence of a hetereogeneous solid catalyst selected from the group consisting of acid clays and acid ion exchange resins, the mole ratio of isoamylene to alpha methyl styrene being between 1:1 and 2:1; the ratio of catalyst to reactants being from 0.1% up to 8% of the total weight of alpha methyl styrene and isoamylene; the reaction temperature being between 75° C. and 250° C.; the reaction pressure being between 50 p.s.i.g. and 300 p.s.i.g.; (ii) reacting the resulting product with propylene oxide in the presence of a catalyst to produce a mixture consisting essentially of indane alkanols according to the reaction:

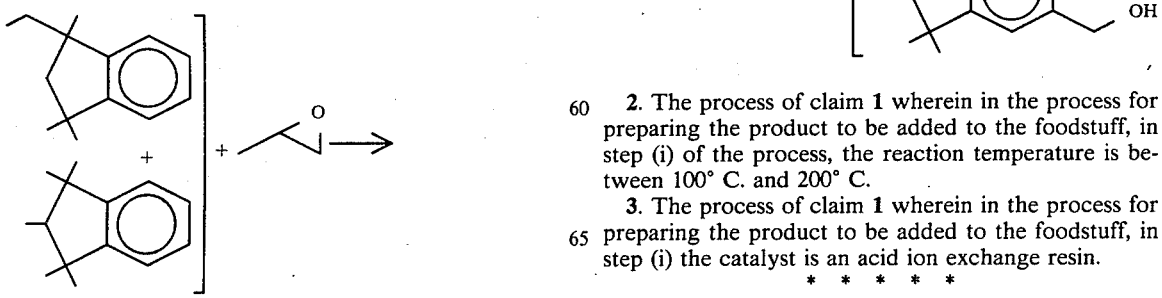

-continued

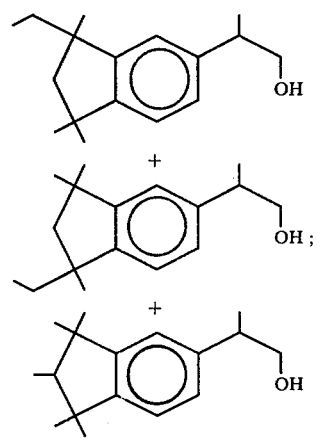

and (iii) reacting the mixture consisting essentially of indane alkanols with a formaldehyde or a formaldehyde source according to the reaction:

2. The process of claim 1 wherein in the process for preparing the product to be added to the foodstuff, in step (i) of the process, the reaction temperature is between 100° C. and 200° C.

3. The process of claim 1 wherein in the process for preparing the product to be added to the foodstuff, in step (i) the catalyst is an acid ion exchange resin.

* * * * *